(12) United States Patent
Wong (10) Patent No.: US 9,579,210 B2
(45) Date of Patent: Feb. 28, 2017

(54) TALAR DOME FIXATION STEM (71) Applicant: Kian-Ming Wong, Lakeland, TN (US)

(72) Inventor: Kian-Ming Wong, Lakeland, TN (US)

(73) Assignee: Wright Medical Technology, Inc., Memphis, TN (US)

( * ) Notice: Subject to any disclaimer, the term of this patent is extended or adjusted under 35 U.S.C. 154(b) by 0 days.

(21) Appl. No.: 14/404,800

(22) PCT Filed: Nov. 7, 2014

(86) PCT No.: PCT/US2014/064572
§ 371 (c)(1),
(2) Date: Dec. 1, 2014

(87) PCT Pub. No.: WO2016/073001
PCT Pub. Date: May 12, 2016

(65) Prior Publication Data
US 2016/0128842 A1 May 12, 2016

(51) Int. Cl.
A61F 2/42 (2006.01)
A61F 2/30 (2006.01)

(52) U.S. Cl.
CPC .... *A61F 2/4202* (2013.01); *A61F 2002/30299* (2013.01); *A61F 2002/30772* (2013.01); *A61F 2002/30878* (2013.01); *A61F 2002/30879* (2013.01); *A61F 2002/30884* (2013.01); *A61F 2002/4207* (2013.01)

(58) Field of Classification Search
CPC ............ A61F 2/4202; A61F 2002/3668; A61F 2002/30884; A61F 2002/30224; A61F 2002/30354

USPC ................. 623/21.18, 17.11–17.16
See application file for complete search history.

(56) References Cited

U.S. PATENT DOCUMENTS

| | | | |
|---|---|---|---|
| 3,872,519 A * | 3/1975 | Giannestras | A61F 2/4202 623/21.18 |
| 3,987,500 A | 10/1976 | Schlein | |
| 4,470,158 A | 9/1984 | Pappas et al. | |
| 4,624,673 A * | 11/1986 | Meyer | A61C 8/005 433/173 |
| 4,759,767 A * | 7/1988 | Lacey | A61F 2/389 623/20.34 |

(Continued)

FOREIGN PATENT DOCUMENTS

| | | |
|---|---|---|
| FR | 2676917 A1 | 12/1992 |
| JP | 2011115440 A | 6/2011 |

(Continued)

OTHER PUBLICATIONS

International Search Report and Written Opinion issued for International patent application PCT/US2014/064572, Aug. 3, 2015, 14 pages.

(Continued)

*Primary Examiner* — Alvin Stewart
(74) *Attorney, Agent, or Firm* — Duane Morris LLP (57) ABSTRACT A talar implant is disclosed. The implant comprises a body comprising a bone contact surface and an articulation surface. A stem extends longitudinally from the bone contact surface. The stem comprises one or more features sized and configured to prevent rotational movement, anterior/posterior movement, and medial/lateral movement. The stem is configured to be received within a hole a talus.

18 Claims, 7 Drawing Sheets

(56) References Cited

U.S. PATENT DOCUMENTS

| | | | |
|---|---|---|---|
| 4,946,379 A | 8/1990 | Berchem | |
| 5,326,366 A * | 7/1994 | Pascarella | A61F 2/4225 623/21.19 |
| 5,413,605 A * | 5/1995 | Ashby | A61F 2/389 623/20.34 |
| 5,480,445 A * | 1/1996 | Burkinshaw | A61F 2/389 623/20.32 |
| 5,489,310 A | 2/1996 | Mikhail | |
| 5,571,203 A * | 11/1996 | Masini | A61F 2/30739 623/22.46 |
| 5,658,341 A * | 8/1997 | Delfosse | A61F 2/38 623/20.32 |
| 6,251,143 B1 * | 6/2001 | Schwartz | A61B 17/064 606/75 |
| 6,379,388 B1 * | 4/2002 | Ensign | A61F 2/389 623/20.21 |
| 6,443,991 B1 * | 9/2002 | Running | A61F 2/3868 623/20.27 |
| 6,506,216 B1 * | 1/2003 | McCue | A61F 2/389 623/20.14 |
| 6,575,986 B2 * | 6/2003 | Overaker | A61B 17/0642 411/508 |
| 6,863,691 B2 | 3/2005 | Short et al. | |
| 7,225,512 B2 * | 6/2007 | Genova | A61B 17/06166 29/7.1 |
| 7,323,012 B1 * | 1/2008 | Stone | A61F 2/4202 623/21.18 |
| 8,641,732 B1 * | 2/2014 | Goraltchouk | A61B 17/06166 606/228 |
| 8,753,402 B2 * | 6/2014 | Winslow | A61B 17/1684 623/19.14 |
| 8,771,365 B2 * | 7/2014 | Bojarski | A61F 2/30942 606/86 R |
| 8,852,286 B2 * | 10/2014 | Cook | A61F 2/30756 623/21.18 |
| 9,144,500 B2 * | 9/2015 | Harding, Jr. | A61F 2/4202 |
| 9,204,971 B2 * | 12/2015 | Rydell | A61B 17/562 |
| 9,216,085 B2 * | 12/2015 | Schwartz | A61F 2/30756 |
| 9,370,429 B1 * | 6/2016 | Sanders | A61F 2/4202 |
| 2002/0120274 A1 * | 8/2002 | Overaker | A61F 2/30756 623/13.14 |
| 2002/0133234 A1 * | 9/2002 | Sotereanos | A61B 17/175 623/23.26 |
| 2003/0204263 A1 * | 10/2003 | Justin | A61F 2/389 623/20.15 |
| 2004/0006394 A1 * | 1/2004 | Lipman | A61F 2/3868 623/20.29 |
| 2004/0122523 A1 * | 6/2004 | Guzman | A61F 2/4202 623/21.18 |
| 2004/0143336 A1 * | 7/2004 | Burkinshaw | A61F 2/3877 623/20.15 |
| 2004/0167631 A1 * | 8/2004 | Luchesi | A61F 2/30771 623/21.18 |
| 2004/0186585 A1 * | 9/2004 | Feiwell | A61F 2/4202 623/21.18 |
| 2005/0154470 A1 * | 7/2005 | Sekel | A61F 2/389 623/20.15 |
| 2005/0182492 A1 * | 8/2005 | Pappas | A61F 2/4202 623/21.18 |
| 2006/0142870 A1 * | 6/2006 | Robinson | A61B 17/14 623/21.18 |
| 2006/0155383 A1 * | 7/2006 | Smith | A61F 2/4081 623/23.51 |
| 2007/0027547 A1 * | 2/2007 | Rydell | A61B 17/562 623/21.18 |
| 2008/0103603 A1 * | 5/2008 | Hintermann | A61F 2/4202 623/20.32 |
| 2008/0306605 A1 * | 12/2008 | Hasselman | A61B 17/15 623/21.18 |
| 2009/0082875 A1 * | 3/2009 | Long | A61F 2/4202 623/21.18 |
| 2009/0265011 A1 * | 10/2009 | Mandell | A61B 17/155 623/20.15 |
| 2009/0265013 A1 * | 10/2009 | Mandell | A61F 2/38 623/20.21 |
| 2010/0057216 A1 * | 3/2010 | Gannoe | A61F 2/4202 623/21.18 |
| 2010/0280625 A1 * | 11/2010 | Sanders | A61F 2/4202 623/21.18 |
| 2010/0298941 A1 * | 11/2010 | Hes | A61F 2/4425 623/17.16 |
| 2011/0035018 A1 * | 2/2011 | Deffenbaugh | A61F 2/389 623/20.28 |
| 2011/0035019 A1 * | 2/2011 | Goswami | A61F 2/4202 623/21.18 |
| 2011/0066248 A1 * | 3/2011 | Ries | A61B 17/1764 623/20.32 |
| 2011/0106268 A1 * | 5/2011 | Deffenbaugh | A61F 2/389 623/20.32 |
| 2011/0295380 A1 * | 12/2011 | Long | A61F 2/4202 623/21.18 |
| 2012/0010718 A1 * | 1/2012 | Still | A61F 2/4202 623/21.18 |
| 2012/0041564 A1 * | 2/2012 | Landon | A61F 2/389 623/20.34 |
| 2012/0046753 A1 * | 2/2012 | Cook | A61F 2/4202 623/21.18 |
| 2012/0109326 A1 * | 5/2012 | Perler | A61F 2/4202 623/21.18 |
| 2012/0245701 A1 * | 9/2012 | Zak | A61F 2/4202 623/21.18 |
| 2013/0041473 A1 * | 2/2013 | Rouyer | A61F 2/4202 623/21.18 |
| 2013/0090739 A1 * | 4/2013 | Linares | A61F 2/4202 623/21.18 |
| 2014/0018814 A1 * | 1/2014 | Gillard | A61F 2/4202 606/93 |
| 2014/0018931 A1 * | 1/2014 | Gillard | A61F 2/30771 623/21.18 |
| 2014/0107794 A1 * | 4/2014 | Deffenbaugh | A61F 2/389 623/20.28 |
| 2014/0128985 A1 * | 5/2014 | Sanders | A61F 2/4225 623/21.18 |
| 2014/0207244 A1 * | 7/2014 | Sanders | A61F 2/4225 623/21.11 |
| 2014/0277538 A1 * | 9/2014 | Sander | A61F 2/30734 623/20.32 |
| 2014/0371867 A1 * | 12/2014 | Schon | A61B 17/1682 623/21.18 |
| 2015/0045902 A1 * | 2/2015 | Perler | A61F 2/4202 623/21.18 |
| 2015/0057761 A1 * | 2/2015 | Smirthwaite | A61F 2/4202 623/21.18 |

FOREIGN PATENT DOCUMENTS

| | | |
|---|---|---|
| WO | 2005/034817 A1 | 4/2005 |
| WO | 2010-039026 A1 | 4/2010 |

OTHER PUBLICATIONS

Patent Examination Report No. 1 issued on Feb. 17, 2016 in connection with corresponding Australian patent application No. 2014331640, 9 pages.

\* cited by examiner

TALAR DOME FIXATION STEM

CROSS REFERENCE TO RELATED APPLICATIONS

This application is a national phase entry under 35 U.S.C. 371 of international patent application No. PCT/US14/64572, the entirety of which is incorporated herein by reference.

BACKGROUND

An ankle joint may become severely damaged and painful due to arthritis, prior ankle surgery, bone fracture, osteoarthritis, and/or one or more additional conditions. Options for treating the injured ankle have included anti-inflammatory and pain medications, braces, physical therapy, joint arthrodesis, and total ankle replacement.

Total ankle replacement generally comprises two or more components—one portion coupled to the tibia and one portion coupled to the talus. The components comprise articulation surfaces sized and configured to mimic the range of motion of the ankle joint. For example, the talar portion may comprise a component sized and configured to mimic the talar dome and the tibial portion may comprise an articulation surface configured to mimic articulation of the tibia.

Installation of the total ankle replacement may comprise forming one or more holes, slots or cuts in a bone. For example, a hole may be drilled through the talus and into the tibia to create a channel for inserting a tibial stem. As another example, slots can be reamed with an end mill or punch having a guide. In some installations, additional bone is removed from the talus to make space for a talar stem extending from the talar portion.

SUMMARY

In some embodiments, a bone implant is disclosed. The bone implant generally comprises a body and a stem. The body comprises a bone contact surface and an articulation surface. The stem extends longitudinally from the bone contact surface. At least one fin is coupled to the stem and the body to provide anterior/posterior stability, rotational stability, medial/lateral stability, and axial resistance.

In some embodiments, a bone implant is disclosed. The bone implant generally comprises a body and a stem. The body comprises a bone contact surface and an articulation surface. The stem extends longitudinally from the bone contact surface. A spline is formed about the stem. The spline is sized and configured to provide anterior/posterior stability, rotational stability, medial/lateral stability, and axial resistance.

In some embodiments, a bone implant is disclosed. The bone implant generally comprises a body and a stem. The body comprises a bone contact surface and an articulation surface. The stem extends longitudinally from the bone contact surface and comprises a triangular stem having a first leg, a second leg, and a third leg. At least one of the first leg, the second leg, the third leg, defines a plurality of serrations formed thereon. The triangular stem and the plurality of serrations provide anterior/posterior stability, rotational stability, medial/lateral stability, and axial resistance.

BRIEF DESCRIPTION OF THE FIGURES

The features and advantages of the present invention will be more fully disclosed in, or rendered obvious by the following detailed description of the preferred embodiments, which are to be considered together with the accompanying drawings wherein like numbers refer to like parts and further wherein.

DETAILED DESCRIPTION

The description of the exemplary embodiments is intended to be read in connection with the accompanying drawings, which are to be considered part of the entire written description. In the description, relative terms such as "lower," "upper," "horizontal," "vertical," "proximal," "distal," "above," "below," "up," "down," "top" and "bottom," as well as derivatives thereof (e.g., "horizontally," "downwardly," "upwardly," etc.) should be construed to refer to the orientation as then described or as shown in the drawing under discussion. These relative terms are for convenience of description and do not require that the apparatus be constructed or operated in a particular orientation. Terms concerning attachments, coupling and the like, such as "connected" and "interconnected," refer to a relationship wherein structures are secured or attached to one another either directly or indirectly through intervening structures, as well as both movable or rigid attachments or relationships, unless expressly described otherwise.

The present disclosure generally provides a bone implant for use with a joint replacement system. The bone implant comprises a body having a bone contact surface and an articulation surface. A stem extends longitudinally from the bone contact surface. The stem comprises one or more features configured to provide rotational, translational, and pull-out resistance to the implant with respect to a bone. The stem and the one or more features are configured to interface with a hole formed in a bone, such as, for example, a talus.

Figure 1:
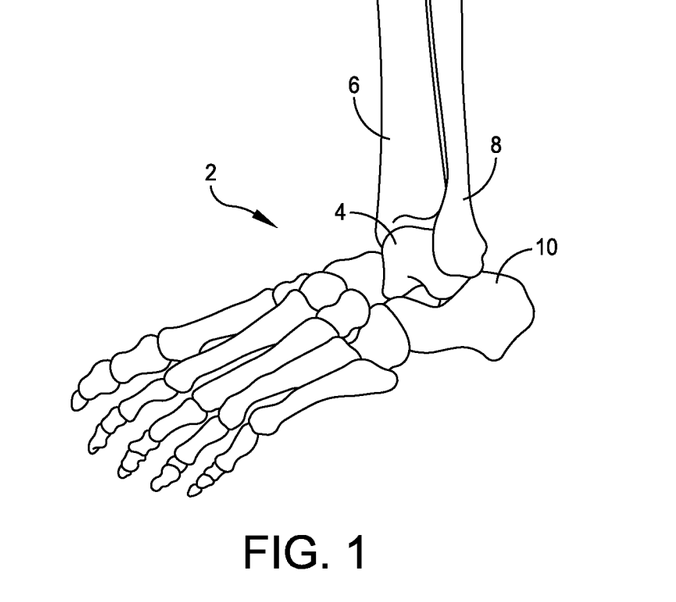
FIG. 1 illustrates an anatomic view of an ankle joint.
Figure 2:
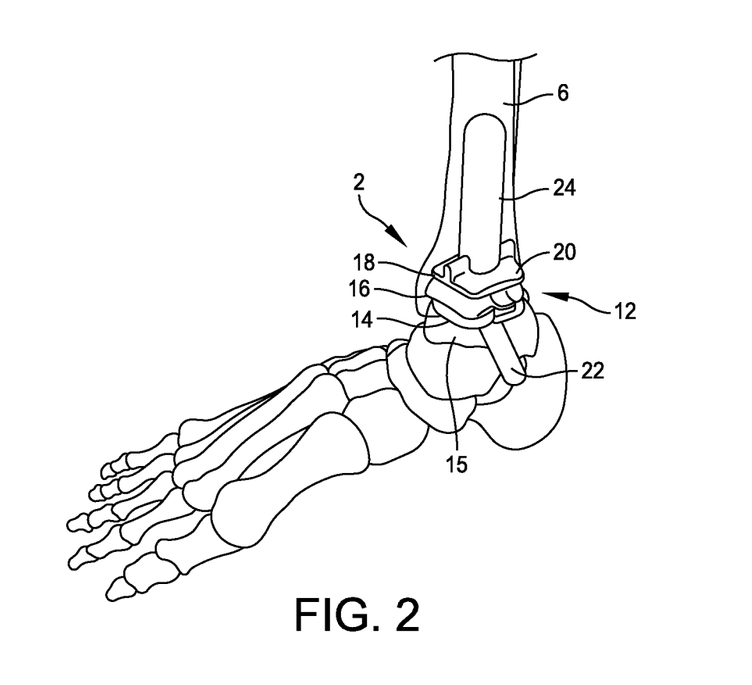
FIG. 2 illustrates one embodiment of an ankle joint having a total ankle replacement system therein.

FIG. 1 illustrates an anatomic view of an ankle joint 2. The ankle joint 2 comprises a talus 4 in contact with a tibia 6 and a fibula 8. A calcaneus 10 is located adjacent to the talus 4. In total ankle replacements, the talus 4 and the tibia 6 may be resected, or cut, to allow insertion of a talar implant and a tibial implant. FIG. 2 illustrates the ankle joint 2 of FIG. 1 having a total ankle replacement system 12 inserted therein.

The total ankle replacement system 12 comprises a talar platform 14 and a tibial platform 18. The talar platform 14 comprises a body 15 defining a talar articulation surface 16

(or talar dome). A stem 22 extends into the talus 4 to anchor the talar platform 14 to the talus 4. The tibial platform 18 is sized and configured for installation into the tibia 6. The tibial platform 18 comprises a body having an articulation surface 20 and a tibial stem 24 extending into the tibia 6 to anchor the tibial platform 18. The talar joint surface 16 and the tibial joint surface 20 are mutually sized and configured to articulate. The joint surfaces 16, 20 replace the natural ankle joint surfaces, which are removed, to restore a range of motion and a height that mimics the natural joint. One or more holes may be formed in the tibia and/or the talus prior to and during insertion of the tibial implant 18 or the talar implant 12. For example, in some embodiments, a hole is drilled starting in the bottom of the talus, extending through the talus and into the tibia. The hole may comprise, for example, a 6 mm hole configured to receive the stem 24 of the tibial platform 18.

The joint surfaces 16, 20 may be made of various materials, such as, for example, polyethylene, high molecular weight polyethylene (HMWPE), rubber, titanium, titanium alloys, chrome cobalt, surgical steel, and/or any other suitable metal, ceramic, sintered glass, artificial bone, and/or any combination thereof. In some embodiments, the joint surfaces 16, 20 may comprise a coated surface. For example, in some embodiments, the joint surfaces 16, 20 may be plasma sprayed with a porous material, such as, for example, a biofoam material. The joint surfaces 16, 20 may comprise different materials. For example, the tibial joint surface 20 may comprise a plastic or other non-metallic material and the talar joint surface 16 may comprise a metal surface. Those skilled in the art will recognize that any suitable combination of materials may be used.

Figure 3:
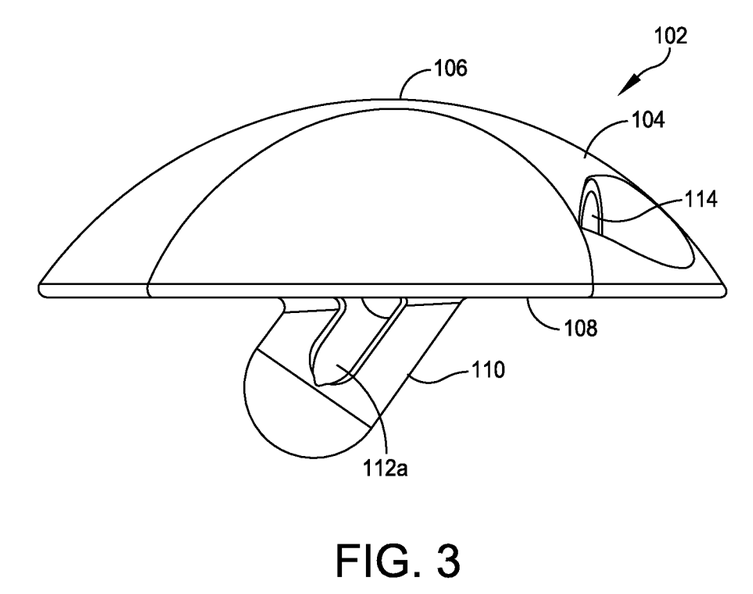
FIG. 3 illustrates a side view of one embodiment of a talar dome comprising a stem having a plurality of fins.

FIG. 3 is a side view of one embodiment of an implant 102 comprising a stem 110 having one or more fins 112a, 112b. The implant 102 comprises a body an articulation surface 106 and a bone contact surface 108. The joint articulation surface 106 is sized and configured to allow articulation of a bone and/or implant in contact with the articulation surface 106. For example, in some embodiments, the implant 102 comprises a talar implant. The articulation surface 106 is sized and configured to allow articulation of a tibia and/or tibial implant in contact with the implant 102 after installation. In other embodiments, the articulation surface 106 may be sized and configured to allow articulation of additional and/or alternative bones and/or implants.

The body 104 further comprises a bone contact surface 108 located opposite from the articulation surface 106. The bone contact surface 108 is configured to interface with a bone surface prepared during surgery. For example, in some embodiments, the bone contact surface 108 is configured to interface with a resected bone surface, such as a resected talus, to couple the implant 102 to the bone. In some embodiments, the bone contact surface 108 comprises a generally planar surface. In other embodiments, the bone contact surface 108 comprises a concave surface. In some embodiments, only a portion of the bone contact surface 108, such as, for example, an outer perimeter, interfaces with the bone surface prepared during surgery. The bone contact surface 108 may comprise a surface lip located at the edge of the implant 102 sized and configured to maintain the implant 102 in a proper location and/or alignment with respect to the bone. In some embodiments, the bone contact surface 108 comprises multiple bone contact points/surfaces.

A stem 110 extends longitudinally at an angle from the bone contact surface 108. The stem 110 is sized and configured to be inserted into a hole formed in the bone during surgery. The stem 110 extends a predetermined distance from the bone contact surface 108. In some embodiments, the stem 110 extends a predetermined distance that is less than, equal to, or greater than a thickness of the body 104. For example, the stem 110 may extend a distance equal to the distance between the articulation surface 106 and the bone contact surface 108 of the body 104. The stem 110 may extend at any suitable angle from the bone contact surface 108. For example, in various embodiments, the stem 110 may extend at an angle of between 0-180 degrees from the bone contact surface 108.

Figure 4:
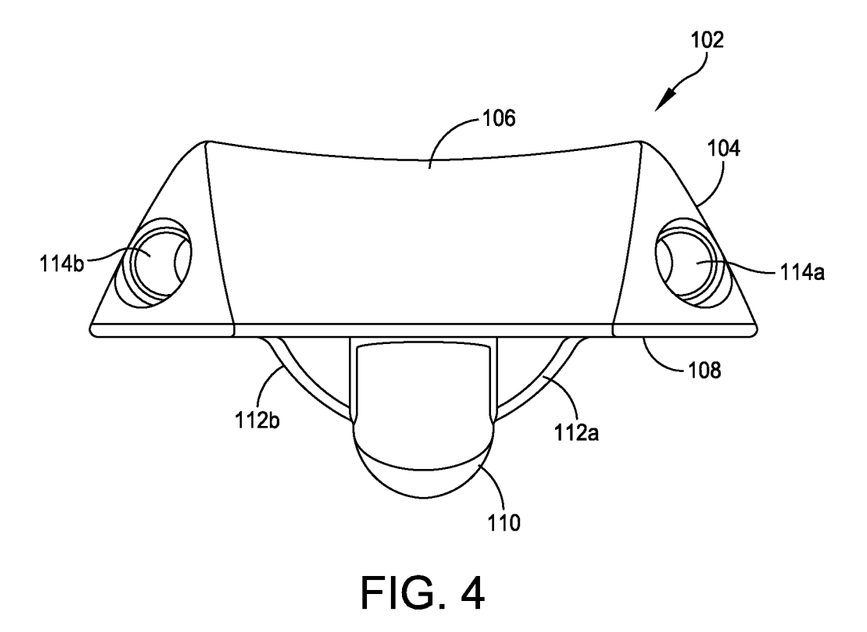
FIG. 4 illustrates a front view of the talar dome of FIG. 3.

The stem 110 comprises one or more features configured to provide rotational, translational, and/or pull-out resistance to the stem 110. In the illustrated embodiment, the stem 110 comprises one or more fins 112a, 112b. The fins 112a, 112b extend from the bone contact surface 108 and the stem 110. The fins 112a, 112b provide anterior/posterior stability, longitudinal stability, and medial/lateral stability to the implant 102 when the implant 102 is coupled to a bone. The fins 112a, 112b are inserted into channels formed in the bone during surgery. For example, in one embodiment, the fins 112a, 112b are inserted into fin channels formed in a talus during a talar resectioning procedure. The fins 112a, 112b contact the side walls of the channels and maintain the implant 102 in a predetermined position and alignment with respect to the bone. FIG. 4 illustrates a front view of the implant 102. In some embodiments, the body 104 of the implant 102 defines one or more holes 114a, 114b sized and configured to receive a handle therein (not shown) to allow manipulation of the talar implant during implantation.

In some embodiments, the implant 102 is coupled to the bone to provide axial resistance. For example, in one embodiment, the implant 102 is cemented to the bone. The implant may be cemented to the bone at the bone contact surface 108 and/or at the stem 110. As another example, in one embodiment, the implant 102 is press-fit into a hole formed in the bone. The hole is sized and configured to receive the stem 110 in a press-fit engagement. The implant 102 may be coupled to the bone by any other suitable method and/or any combination of methods, such as, for example, being cemented and press-fit into engagement with the bone.

Figure 5:
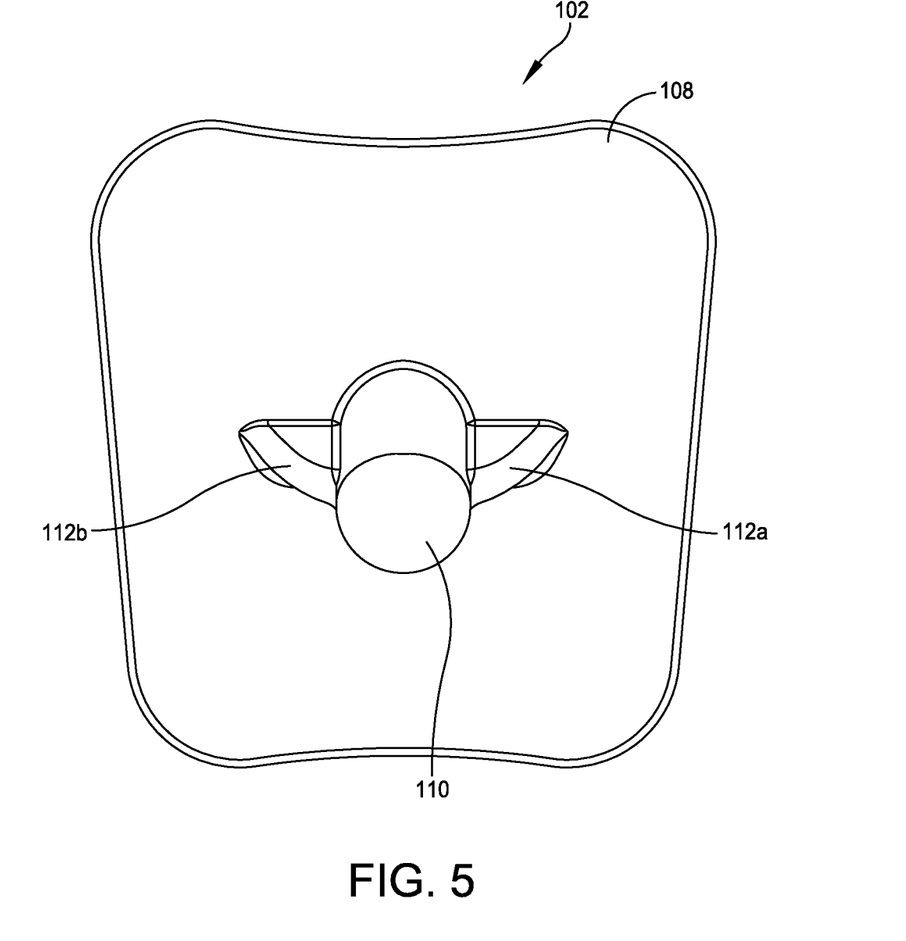
FIG. 5 illustrates a bottom view of the talar dome of FIG. 3.

FIG. 5 illustrates a bottom view of the implant 102. As shown in FIG. 4, the stem 110 and the fins 112a, 112b extend longitudinally from the bone contact surface 108. Although two fins 112a, 112b are illustrated, it will be recognized that the implant 102 may comprise any number of one or more fins. The fins 112a, 122b comprise semi-circular sections extending from the bone contact surface 108 to the stem 110. Although the fins 112a, 112b are illustrates as semi-circular, it will be recognized that the fins may comprise any suitable shape such, as for example, rectangular, triangular, and/or any other suitable shape.

Figure 6:
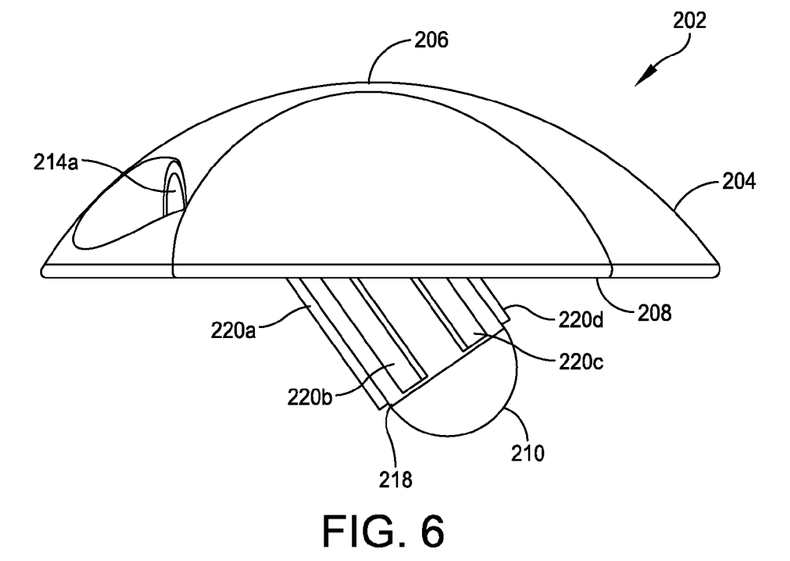
FIG. 6 illustrates a side view of one embodiment of a talar dome comprising a stem having a spline formed thereon.
Figure 7:
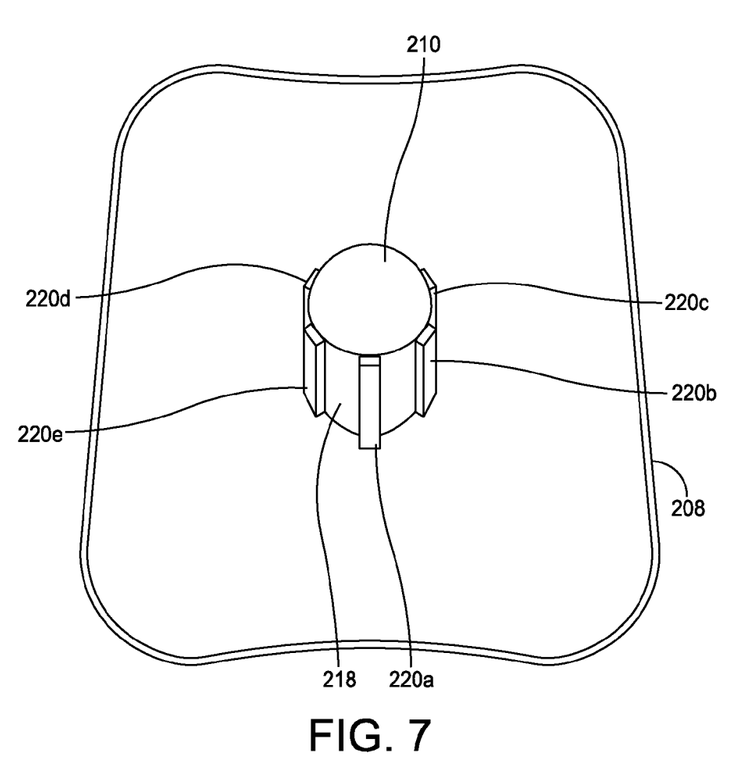
FIG. 7 illustrates a bottom view of the talar dome of FIG. 6.

FIG. 6 illustrates a side view of one embodiment of an implant 202 comprising a stem 210 having a spline 218 formed thereon. FIG. 7 illustrates a bottom view of the implant 202. The implant 202 is similar to the implant 102 described with reference of FIGS. 3-5 above. The implant 202 comprises an implant body 204. The implant body 204 defines an articulation surface 206 and a bone contact surface 208. A stem 210 extends longitudinally from the bone contact surface 208. The stem 210 comprise one or more features configured to provide rotational, translational, and/or pull-out resistance to the implant 202 with respect to a bone.

In the illustrated embodiment, the one or more features comprise a spline 218. The spline 218 comprises a plurality of teeth 220a-220e. The plurality of teeth 220a-220e are configured to provide anterior/posterior stability, rotational stability, and medial/lateral stability. In some embodiments, the plurality of teeth 220a-220e are configured to interface with a plurality of grooves formed in a hole in the bone. The teeth 220a-220e interface with the grooves formed in the hole to prevent movement and rotation of the implant 202 with respect to the bone.

Figure 8:
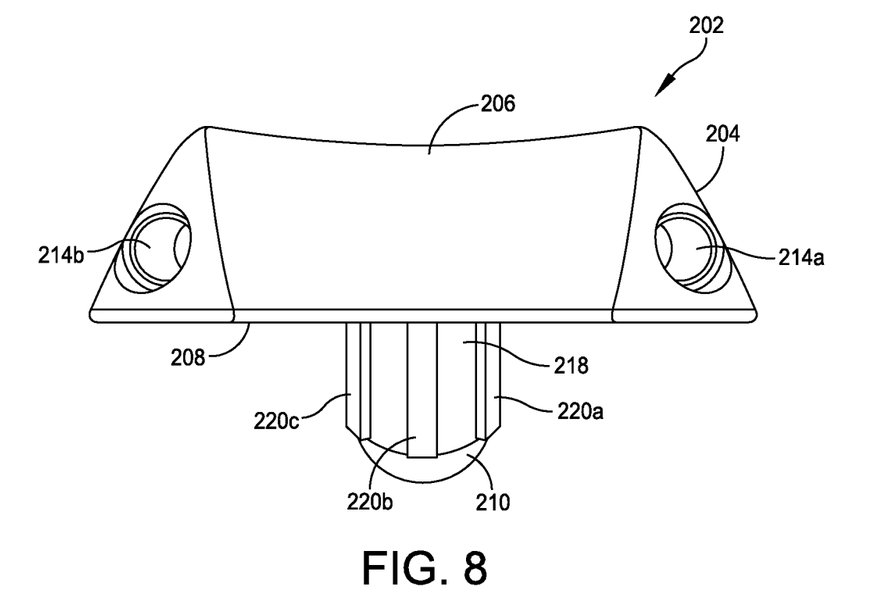
FIG. 8 illustrates a front view of the talar dome of FIG. 6.

FIG. 8 illustrates a front view of the implant 202. The body 204 of the implant 202 may define one or more holes 214a, 214b sized and configured to couple the implant 202 to one or more additional implants. For example, in some embodiments, the implant 202 comprises a talar dome platform configured to couple to a talus and to receive a talar dome thereon. The plurality of holes 214a, 214b are configured to receive one or more mating features of the talar dome therein to mate the talar dome to the implant 202. In other embodiments, the plurality of holes 214a, 214b may be coupled to an adjacent implant, such as, for example, a tibial implant, to maintain the implant 202 and the adjacent implant in a predetermined spacing/alignment.

Figure 9:
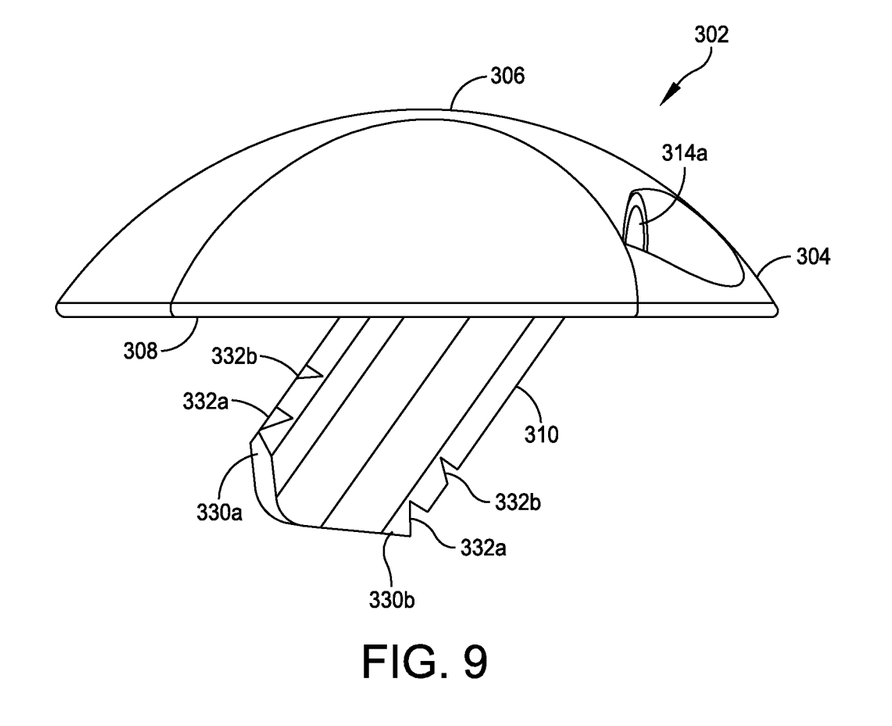
FIG. 9 illustrates a side view of one embodiment of a talar dome comprising a triangular stem defining a plurality of serrated blades.
Figure 10:
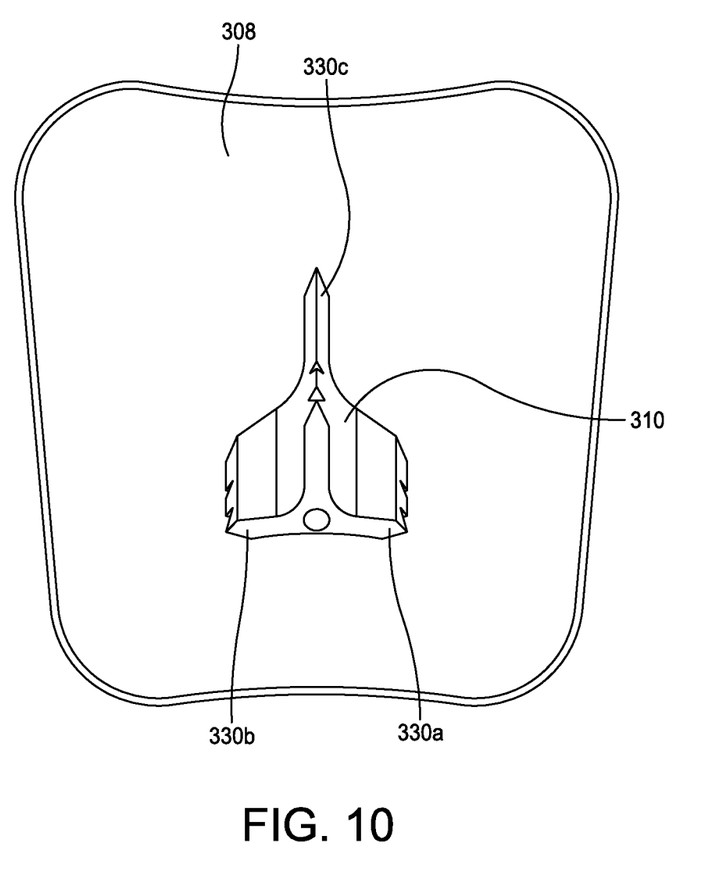
FIG. 10 illustrates an angled bottom view of the talar dome of FIG. 9.

FIG. 9 illustrates a side view of one embodiment of an implant 302 comprising a triangular stem 310 having a plurality of serrations 332 formed thereon. FIG. 10 illustrates a bottom view of the implant 302. The implant 302 is similar to the implant 102 described with reference of FIGS. 3-5 above. The implant 302 comprises an implant body 304. The implant body 304 defines an articulation surface 306 and a bone contact surface 308. A stem 310 extends longitudinally from the bone contact surface 308. The stem 310 comprise one or more features configured to provide rotational, translational, and/or pull-out resistance to the implant 302 with respect to a bone.

The triangular stem 310 comprises a first leg 330a, a second leg 330b, and a third leg 330c. In some embodiments, the plurality of legs 330a-330c are equally spaced about a circumference of the stem 310. Each of the plurality of legs 330a-330c comprises a plurality of serrations 332 formed on an outer edge of the leg 330a-330c. The stem 310 may be inserted into a hole formed in a bone, such as, for example, a talus. The hole may comprise any suitable shape for receiving the stem 310, such as, for example, a triangular, square, round, or other cross-sectional shape. The plurality of legs 330a-330c prevent anterior/posterior motion, rotational motion, and/or medial/lateral motion. The plurality of serrations 332 are configured to provide pull-out resistance to the stem 310.

FIG. 10 is an angled bottom view of the implant 302. The angled bottom view illustrates the serrated portions 332 of each of the legs 330a-330c. The legs 330a-330c each extend longitudinally from the bone contact surface 308. In the illustrated embodiment, the legs 330a-330c are equally spaced about a circumference defined by the stem 310. In other embodiments, the each of the legs 330a-330c may be separated from each of the other legs by unequal distances and/or angles. For example, the first leg 330a may be separated from the second leg by a first angle and from the third leg by a second angle. The second and third legs may be separated by a third angle.

Figure 11:
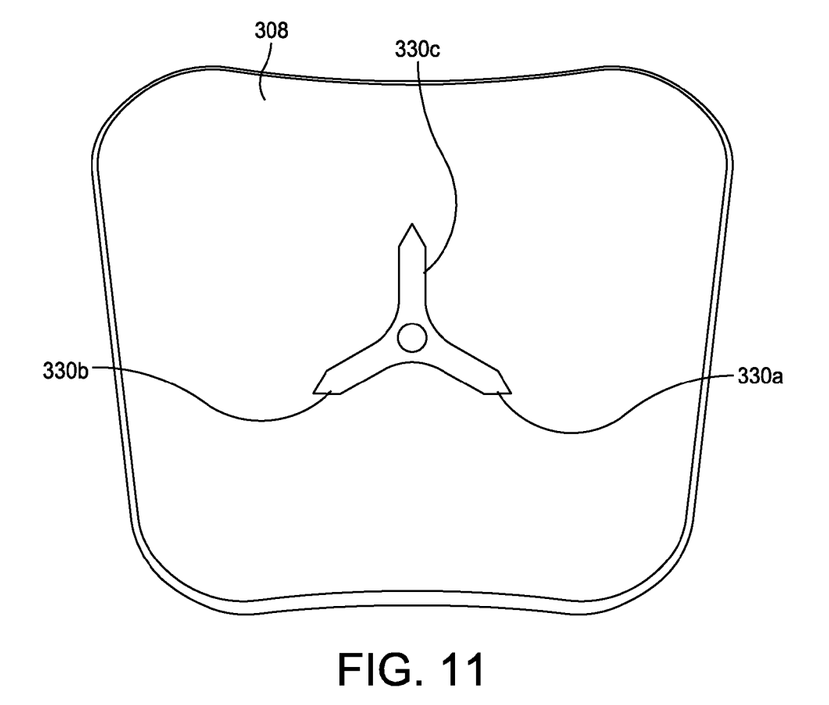
FIG. 11 illustrates a bottom view of the talar dome of FIG. 9.

FIG. 11 illustrates a bottom view of the implant 302. The bottom-view illustrates the triangular, or christmas-tree shape, of the stem 310. The shape of the stem 310 provides anterior/posterior stability, rotational stability, and medial/lateral stability. In some embodiments, the edges of the legs 330a-330c are sharp to allow the edges 330a-330c to bite or dig into a bone to provide further stability. The serrations 332 may also be sharp in order to provide additional stability and pull-out resistance.

Figure 12:
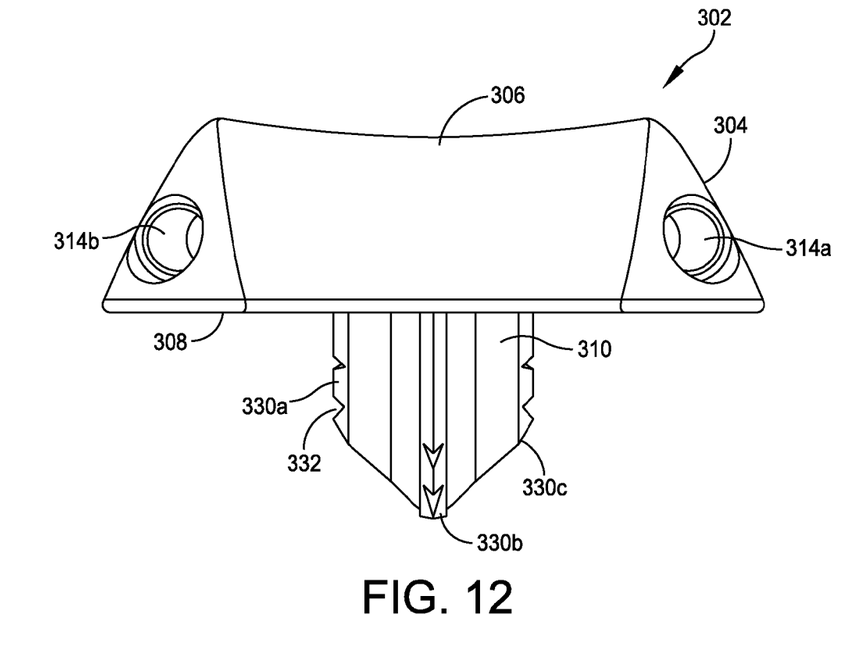
FIG. 12 illustrates a front view of the talar dome of FIG. 9.

FIG. 12 illustrates a front view of the implant 302. The body 304 of the implant 302 may define one or more holes 314a, 314b sized and configured to couple the implant 302 to one or more additional implants. For example, in some embodiments, the implant 302 comprises a talar dome platform configured to couple to a talus and to receive a talar dome thereon. The plurality of holes 314a, 314b are configured to receive one or more mating features of the talar dome therein to mate the talar dome to the implant 302. In other embodiments, the plurality of holes 314a, 314b may be coupled to an adjacent implant, such as, for example, a tibial implant, to maintain the implant 302 and the adjacent implant in a predetermined spacing/alignment.

In various embodiments, an implant is disclosed. The implant a body having a bone contact surface and an articulation surface. A stem extends longitudinally from the bone contact surface. At least one fin is coupled to the stem and the body.

In some embodiments, the at least one fin is sized and configured to be received within a channel formed in a bone to prevent anterior/posterior movement, rotational movement, and medial/lateral movement.

In some embodiments, the at least one fin comprises a wedge shaped fin.

In some embodiments, the wedge-shaped fin comprises a first flat edge coupled to the stem, a second flat edge coupled to the body, and an arcuate edge extending from an end of the first flat edge to an end of the second flat edge.

In some embodiments, the implant comprises a first fin located on a first side of the stem and a second fin located on a second side of the fin.

In some embodiments, the body defines at least one instrument hole sized and configured to receive an instrument for deploying the implant therein.

In some embodiments, the stem extends a predetermined distance from the body, and wherein the predetermined distance is less than a thickness of the body.

In some embodiments, the articulation surface is sized and configured to mimic a talar dome.

In various embodiments, an implant is disclosed. The implant comprises a body having a bone contact surface and an articulation surface. A stem extends longitudinally from the bone contact surface. A spline is formed about the stem.

In some embodiments, the spline is sized and configured to be received within a channel formed in a bone to prevent anterior/posterior movement, rotational movement, and medial/lateral movement.

In some embodiments, the spline comprises a plurality of equally spaced teeth disposed about a circumference of the stem.

In some embodiments, the body defines at least one instrument hole sized and configured to receive an instrument for deploying the implant therein.

In some embodiments, the stem extends a predetermined distance from the body, and wherein the predetermined distance is less than a thickness of the body.

In some embodiments, the articulation surface is sized and configured to mimic a talar dome.

In various embodiments, an implant is disclosed. The implant comprises a body having a bone contact surface and an articulation surface. A triangular stem having a first leg, a second leg, and a third leg extends longitudinally from the body. At least one of the first leg, the second leg, or the third leg, defines a plurality of serrations formed thereon.

In some embodiments, the triangular stem is sized and configured to prevent rotational movement, anterior/posterior movement, and medial/lateral movement, and wherein the plurality of serrations provide pull-out resistance to the stem.

In some embodiments, each of the first leg, the second leg, and the third leg comprise a sharpened edge.

In some embodiments, the body defines at least one instrument hole sized and configured to receive an instrument for deploying the implant therein.

In some embodiments, the stem extends a predetermined distance from the body, and wherein the predetermined distance is less than a thickness of the body.

In some embodiments, the articulation surface is sized and configured to mimic a talar dome.

Although the subject matter has been described in terms of exemplary embodiments, it is not limited thereto. Rather, the appended claims should be construed broadly, to include other variants and embodiments, which may be made by those skilled in the art.

What is claimed is:

1. An implant, comprising:
   a body comprising a bone contact surface and an articulation surface, the bone contact surface being planar;
   a stem extending from the at least one bone contact surface, the stem having a longitudinal axis, wherein the stem extends a predetermined distance from the body, and wherein the predetermined distance is less than a thickness of the body; and
   at least one fin coupled to the stem and the body, wherein the longitudinal axis and the at least one fin are oriented at an oblique angle relative to the bone contact surface.

2. The implant of claim 1, wherein the at least one fin is sized and configured to be received within a channel formed in a bone to prevent anterior/posterior movement, rotational movement, and medial/lateral movement.

3. The implant of claim 2, wherein the at least one fin comprises a wedge shaped fin.

4. The implant of claim 3, wherein the wedge-shaped fin comprises a first flat edge coupled to the stem, a second flat edge coupled to the body, and an arcuate edge extending from an end of the first flat edge to an end of the second flat edge.

5. The implant of claim 2, comprising a first fin located on a first side of the stem and a second fin located on a second side of the stem.

6. The implant of claim 1, wherein the body defines at least one instrument hole sized and configured to receive an instrument for deploying the implant therein.

7. The implant of claim 1, comprising a biofoam coating formed on the articulation surface of the body.

8. An implant, comprising:
   a body comprising a bone contact surface and an articulation surface wherein the articulation surface is sized and configured to mimic a talar dome, and the implant is part of a total ankle replacement, which further comprises a tibial implant having a tibial articulation surface and a tibial stem configured to extend into the tibia, the bone contact surface being planar;
   a stem extending from the at least one bone contact surface, the stem having a longitudinal axis; and
   at least one fin coupled to the stem and the body, wherein the longitudinal axis and the at least one fin are oriented at an oblique angle relative to the bone contact surface.

9. An implant, comprising:
   a body comprising at least one bone contact surface and an articulation surface, the bone contact surface being planar;
   a stem extending from the at least one bone contact surface, the stem shaped as a circular cylinder having a circumference and further wherein the stem extends a predetermined distance from the body, and wherein the predetermined distance is less than a thickness of the body; and
   a spline formed about the stem, the spline comprising a plurality of rectangular teeth extending along the length of the stem, the teeth equally spaced about the entire circumference.

10. The implant of claim 9, wherein the spline is sized and configured to be received within a channel formed in a bone to prevent anterior/posterior movement, rotational movement, and medial/lateral movement.

11. The implant of claim 10, wherein the spline and a longitudinal axis of the stem are oriented at an oblique angle relative to the bone contact surface.

12. The implant of claim 9, wherein the body defines at least one instrument hole sized and configured to receive an instrument for deploying the implant therein.

13. An implant, comprising:
   a body comprising at least one bone contact surface and an articulation surface wherein the articulation surface is sized and configured to mimic a talar dome, and the implant is part of a total ankle replacement, which further comprises a tibial implant having a tibial articulation surface and a tibial stem configured to extend into the tibia, the bone contact surface being planar;
   a stem extending from the at least one bone contact surface, the stem shaped as a circular cylinder having a circumference; and
   a spline formed about the stem, the spline comprising a plurality of rectangular teeth extending along the length of the stem, the teeth equally spaced about the entire circumference.

14. An implant, comprising:
   a body comprising a bone contact surface and an articulation surface, the bone contact surface being planar;
   a Y-shaped stem having a first leg, a second leg, and a third leg extending from the body a predetermined distance from the body, and wherein the predetermined distance is less than a thickness of the body, the Y-shaped stem having a longitudinal axis, wherein at least one of the first leg, the second leg, or the third leg has an edge having a plurality of serrations formed thereon, and the longitudinal axis is oriented at an oblique angle relative to the bone contact surface, and the edge having the plurality of serrations is parallel to the longitudinal axis.

15. The implant of claim 14, wherein the Y-shaped stem is sized and configured to prevent rotational movement, anterior/posterior movement, and medial/lateral movement, and wherein the plurality of serrations provide pull-out resistance to the stem.

16. The implant of claim 15, wherein each of the first leg, the second leg, and the third leg comprise a respective edge, each edge being sharpened, each edge having two of the plurality of serrations with a portion of the sharpened edge parallel to the longitudinal axis therebetween.

17. The implant of claim 14, wherein the body defines at least one instrument hole sized and configured to receive an instrument for deploying the implant therein.

18. An implant, comprising:
a body comprising a bone contact surface and an articulation surface wherein the articulation surface is sized and configured to mimic a talar dome, and the implant is part of a total ankle replacement, which further comprises a tibial implant having a tibial articulation surface and a tibial stem configured to extend into the tibia, the bone contact surface being planar;
a Y-shaped stem having a first leg, a second leg, and a third leg extending from the body, the Y-shaped stem having a longitudinal axis, wherein at least one of the first leg, the second leg, or the third leg has an edge having a plurality of serrations formed thereon, and the longitudinal axis is oriented at an oblique angle relative to the bone contact surface, and the edge having the plurality of serrations is parallel to the longitudinal axis.

\* \* \* \* \*